United States Patent [19]

Scarberry

[11] 4,231,365
[45] Nov. 4, 1980

[54] EMERGENCY RESUSCITATION APPARATUS

[76] Inventor: Eugene N. Scarberry, 2834 Durban, Houston, Tex. 77043

[21] Appl. No.: 873,517

[22] Filed: Jan. 30, 1978

[51] Int. Cl.³ .............................................. A61M 16/00
[52] U.S. Cl. .............................................. 128/207.15
[58] Field of Search ............... 128/351, 349 R, 349 B, 128/349 BV, 350 R, 145.5, 145.8, 208, 276, 207.14, 207.15

[56] References Cited

U.S. PATENT DOCUMENTS

| | | | |
|---|---|---|---|
| 2,112,666 | 3/1938 | Fennell | 128/350 R |
| 3,334,628 | 8/1967 | Saemann et al. | 128/276 |
| 3,683,908 | 8/1972 | Don Michael et al. | 128/145.7 |
| 3,717,147 | 2/1973 | Flynn | 128/145.5 X |
| 3,730,179 | 5/1973 | Williams | 128/351 X |
| 3,874,377 | 4/1975 | Davidson | 128/145.5 |
| 3,957,055 | 5/1976 | Linder et al. | 128/351 |
| 3,985,141 | 10/1976 | Stanley et al. | 128/351 |
| 3,993,059 | 11/1976 | Sjostrand | 128/145.8 |
| 4,064,882 | 12/1977 | Johnson et al. | 128/351 |
| 4,090,518 | 5/1978 | Elam | 128/351 X |
| 4,091,816 | 5/1978 | Elam | 128/351 |
| 4,150,676 | 4/1979 | Jackson | 128/351 |
| 4,155,365 | 5/1979 | Boslan | 128/351 |

OTHER PUBLICATIONS

Elam et al., Airway Management with the Esophageal Pharyngeal Airway, (1977) pp. 65-72, Chapter 9 of Advances in Cardiopulmonary Resuscitation.

*Primary Examiner*—Henry J. Recla
*Attorney, Agent, or Firm*—Bard & Groves

[57] ABSTRACT

An emergency resuscitation apparatus is provided by an endotracheal tube having a tracheal obturator and a second expandable cuff for sealing against the pharyngeal tissues to provide an alternate sealing means for respiratory fluids if the blind intubation is not successful. A laryngeal tube passes through this pharyngeal obturator for alternatively introducing respiratory fluids into the lungs through the larynx. The endotracheal tube may also be used as an esophageal obturator and inserted without the intubating guide means. The endotracheal and laryngeal tubes may be individually accessed from outside the patient. An inflation system is provided to expand the cuffs. When low pressure cuffs are used, a mouthpiece is provided for inflating the cuffs by breathing. A face shield supports the extending tubes and insures intubation to a correct depth.

4 Claims, 4 Drawing Figures

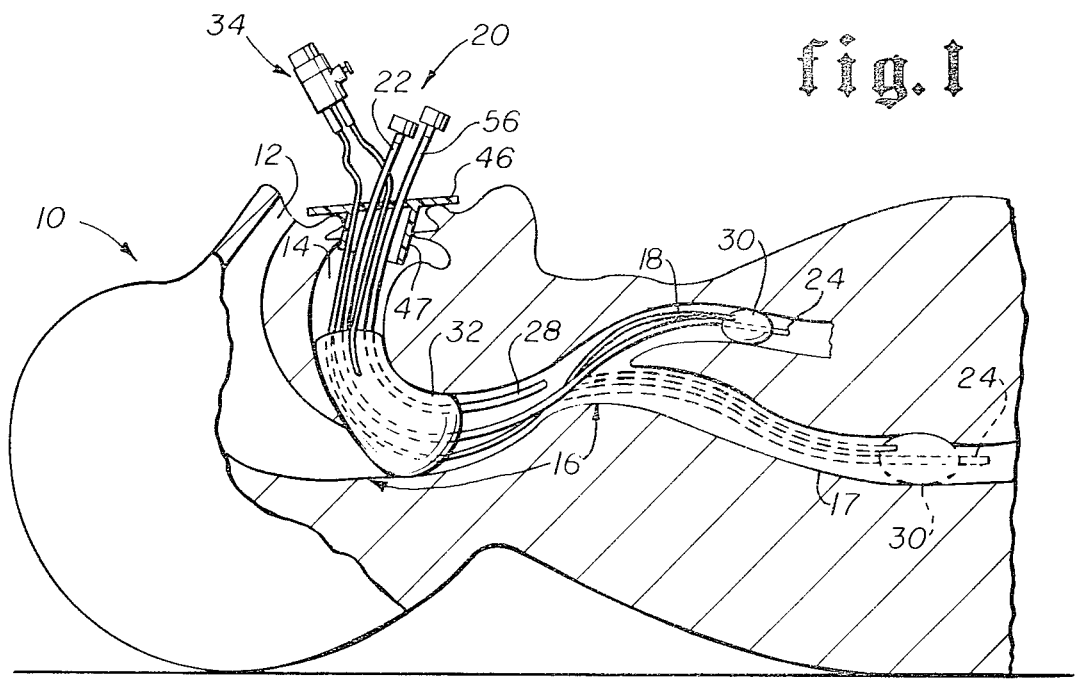
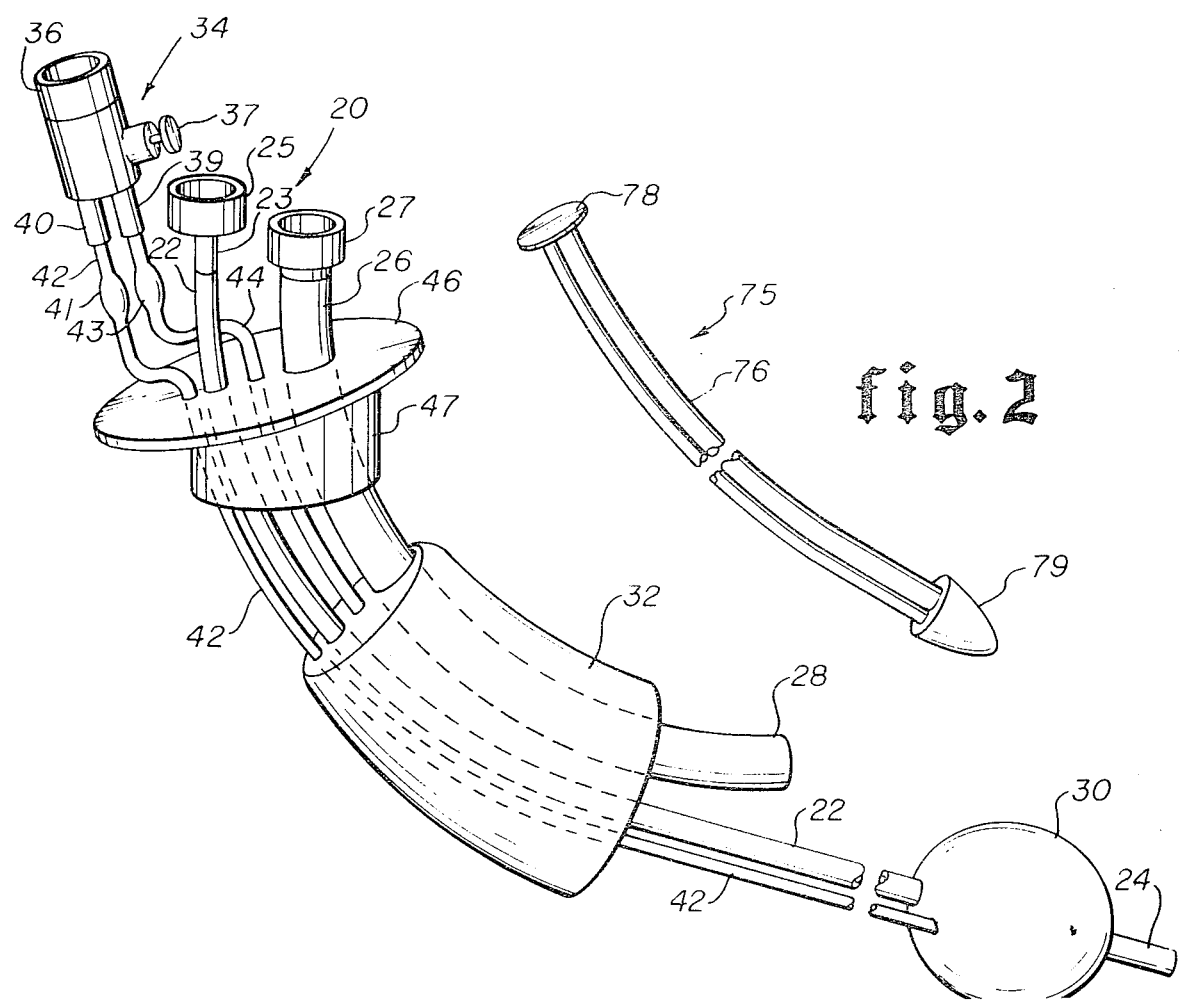

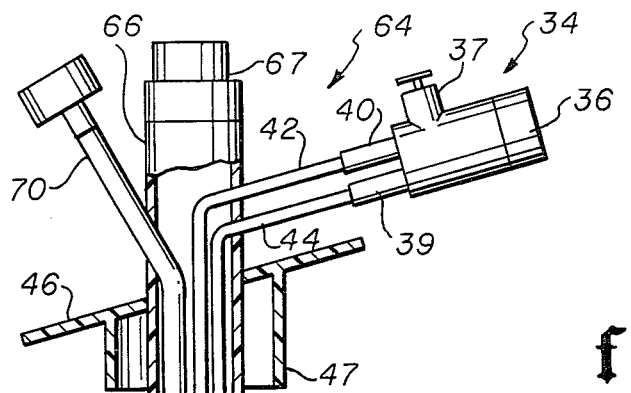
fig.3
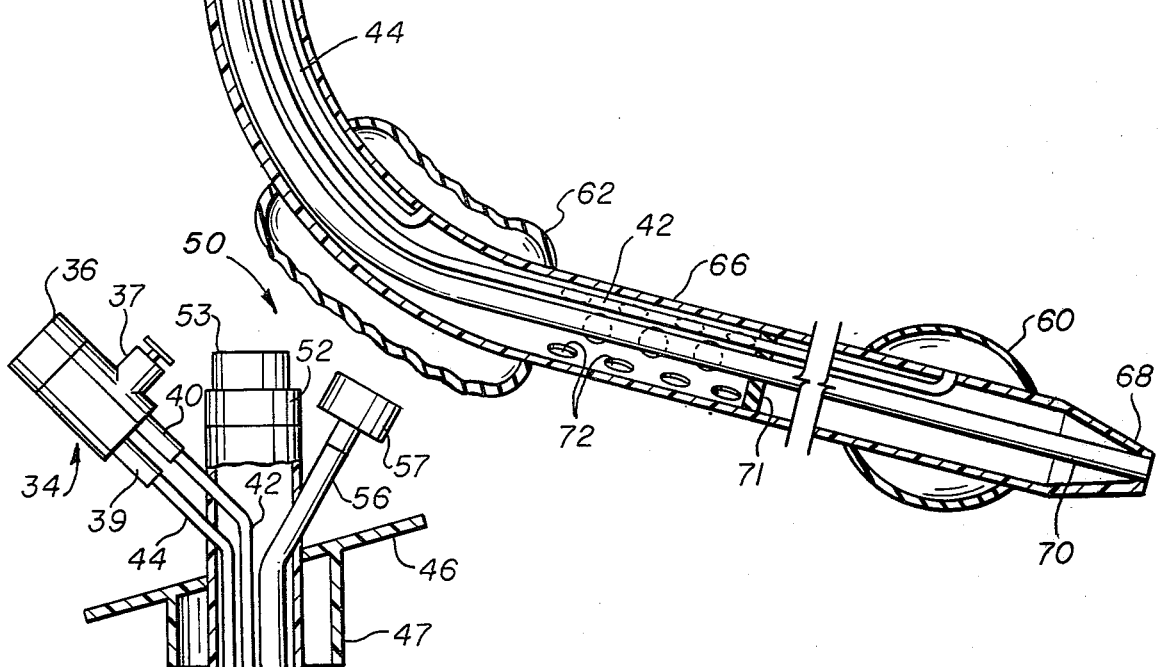
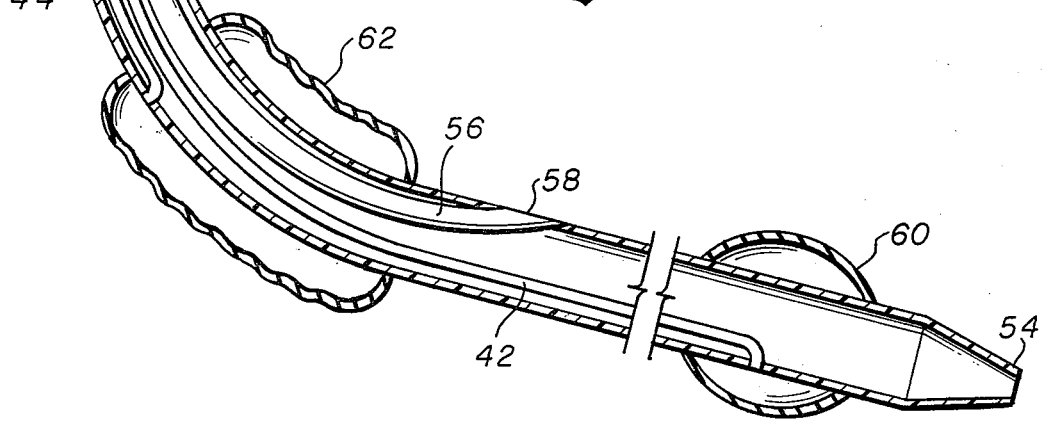
fig.4

EMERGENCY RESUSCITATION APPARATUS

FIELD OF THE INVENTION

This invention relates to emergency medical apparatus and, more particularly, to emergency apparatus for introducing a fluid into the lungs for artificial respiration.

BACKGROUND OF THE INVENTION

Artificial respiration or resuscitation techniques now being used to revive a victim without normal respiratory function involve the introduction of a fluid such as oxygen or air directly into the patient. In the most rudimentary form, this is accomplished by "mouth-to-mouth" respiration where a medical attentant or the like exhales directly into the mouth of the patient, thereby forcing air into the lungs.

A more satisfactory technique involves intubation, where a hollow tube is inserted through the mouth and into the proximity of the larynx. Yet another improvement involves sealing off the esophagus in order to prevent diversion of respiration effort to inflation of the stomach. In addition, an open esophagus can result in aspiration of the stomach contents through the esophagus into the mouth and throat, and subsequently into the respiratory passages. The occurrence of such backflow could result in the inability of the lungs to receive the fluid needed for respiration.

One prior art device is an endotracheal tube which is inserted through the mouth of the patient, through the laryngeal region and into the patient's trachea. The respirating fluid is then introduced almost directly into the lungs without significant diversion to the stomach. Insertion of the endotracheal tube requires some skill, however, and a laryngoscope is required for accurate intubation. Inserting an endotracheal tube without a laryngoscope, "blind" insertion does not always succeed and this insertion is not a technique which is recommended for use by emergency medical technicians at locations remote from a hospital.

Yet another prior art device, depicted in U.S. Pat. No. 3,683,908, embodies an esophageal obturator where an elongated tube carries an expandable device into the patient's esophagus, the expandable member to obturate, or block off, the esophagus. The elongated member includes internal openings to provide for the introduction of air into the laryngeal region. Backflow of air from the laryngeal region through the nose and mouth passages is prevented by the use of a face shield which is forced against the contours of the face to seal about the face. Such a device requires constant attendance to maintain the seal between the patient's face and the apparatus shield and, if a respirator machine is not available, two people are required to respirate the patient.

Still another prior art device is described in an article by Elam et al, *Advances in Cardiopulmonary Resuscitation,* 1977, pages 65-72, wherein a esophageal obturator is combined with a pharyngeal cuff to obviate the need for a sealing face mask. A pharyngeal cuff with a single tube may also be used to ventilate the laryngeal region. No attempt is made to intubate the trachea and, indeed, such intubation is taught to be undesirable.

U.S. Pat. No. 3,874,377 to Davidson discloses an insertable tube for use in sealing either the esophagus or the trachea. A rotating valve-like member permits fluid introduction through either the end of the inserted tube or at an upper location proximate to the patient's oral region. Fluid back flow is prevented by the use of a sealing face mask, as hereinabove described.

The disadvantages of the prior art are overcome by the present invention, however, and improved apparatus for emergency artificial respiration are provided for sealing the patient's airways and introducing air into the lungs.

SUMMARY OF THE INVENTION

In a preferred embodiment of the present invention, an endotracheal tube having a stylet bullet guide preformed to enter the region adjacent the trachea and having an obturator is provided for blind intubation of the trachea where emergency resuscitation is required. A pharyngeal obturator is provided for sealing the upper portion of a patient's airway to prevent the flow of fluids back through the pharynx and out the mouth and nose passages if the blind endotracheal intubation does not succeed. A duct is provided through the pharyngeal cuff for introducing respiratory fluids into the laryngeal region of the patient when the pharyngeal cuff is inflated. If desired, the endotracheal tube may be inserted without the bullet guide and serve as an esophageal obturator to seal the interior of the esophagus so that respiration fluid is confined exclusively to the lungs.

A face shield may be provided to support and position the various tubes inserted into the patient and to insure insertion to the proper location. The face shield is not required to seal about the facial contours but is sized to preclude ingestion through the mouth. The shield is also more aesthetically pleasing in the event expired air is used as the respiratory fluid.

The endotracheal tube may be inserted alternatively into the esophagus to communicate with the stomach to provide for the introduction of fluids into the stomach or the release of gases and/or fluids from the stomach if desired. Such a device may conveniently have a cap or a pressure-indicator balloon over the outer end which would indicate the presence of fluid inside the tube from the stomach region.

The laryngeal and pharyngeal obturators are preferably inflatable members which may be inflated by merely blowing into the members through a suitable mouthpiece. The mouthpiece may be provided with a pressure relief valve to prevent over-pressurizing the obturators and damaging the surrounding tissue. Further, supply lines leading to the inflatable obturators may be equippped with check valves for maintaining fluid inside the obturators until the check valves are open to release the fluid.

It is a primary feature of the present invention to provide an endotracheal tube in an emergency resuscitation apparatus which may be blindly intubated.

It is another feature of the present invention to combine an endotracheal tube and pharyngeal obturator to insure that respiratory fluid is confined to the lungs.

It is yet another feature of the present invention to provide an emergency resuscitation device which can be utilized by emergency medical personnel at locations remote from a hospital.

Yet another feature of the present invention is to provide an emergency medical resuscitation apparatus which can be operated by only one person if manual respiration is required or left substantially unattended if automatic respiration equipment is available.

Still another feature of the present invention is to employ inflatable members as obturators which may be inflated by the human breath to sealingly engage surrounding tissue without damage to that tissue.

These and other features and advantages of the present invention will become apparent from the following detailed description, wherein reference is made to the figures in the accompanying drawings.

IN THE DRAWINGS

FIG. 1 is a pictorial illustration, partly in cross section, showing one embodiment of the present invention properly inserted into a patient.

FIG. 2 is a pictorial view of one embodiment of the emergency apparatus.

FIG. 3 is a cross-sectional view of a second embodiment of the emergency apparatus.

FIG. 4 is a cross-sectional view of a third embodiment of the emergency apparatus.

DETAILED DESCRIPTION OF THE DRAWINGS

Referring now to FIG. 1, there may be seen a pictorial view, partly in cross section, of an endotracheal airway 20 properly inserted in patient 10. A pharyngeal cuff 32 has been inserted into the pharynx at a location which effectively blocks both nasal passage 12 and oral passage 14 and, if inflated, prevents the flow of fluids from these passages into patient 10. A laryngeal tube 56 is provided with an opening adjacent inner end 28 for the purpose of introducing a respiratory fluid into the trachea 18 of patient 10. Laryngeal tube 56 passes adjacent the inflated pharyngeal cuff 32. Endotracheal tube 22 is provided for the primary purpose of introducing respiratory fluid into the patient's trachea.

Tracheal cuff 30 and pharyngeal cuff 32 may conveniently be expanded by introducing an inflating fluid through cuff inflator means 34 which is interconnected with inflatable cuffs 30 and 32. Face shield 46 is placed over a portion of the face of patient 10 and serves to properly position laryngeal tube 56 and endotracheal tube 22 within patient 10. Further, shield 46 insures that none of the apparatus is ingested by patient 10. A teeth shield 47 may be provided to preclude damage to the tubular members from voluntary or involuntary reflex movement by the mouth.

In FIG. 1, endotracheal tube 22 is properly in the trachea and inner end 24 serves to introduce respiratory fluid into the lungs. Tracheal cuff 30 seals the trachea against escape of the respiratory fluid. Proper insertion is accomplished by inserting a relatively stiff stylet bullet guide (see FIG. 2) into tube 22 where the stylet is preshaped to enhance blind entry of inner end 24 into the trachea. If inner end 24 misses the trachea, it will enter the esophagus 17 (see dashed lines) and be available as an esophageal obturator as hereinafter discussed.

It may be seen from FIG. 1 that pharyngeal cuff 32 is inserted adjacent a portion of the pharynx 16 and to a position to effectively block both oral passage 14 and nasal passage 12. The pharynx comprises the soft, muscular and membranous cavity portion of the alimentary canal leading from the mouth and nasal passages to the larynx and esophagus. It is desired that pharyngeal cuff 32 seal both the oral and nasal regions of pharynx 16. Accordingly, it is desired to utilize a relatively low pressure to inflate pharyngeal cuff 32 in order to prevent damage to these soft tissues.

When properly inserted, emergency endotracheal airway 20 serves to seal the interior of trachea by inflating tracheal obturator 30 to engage the interior of trachea 18 and/or to seal the pharynx 16, if needed, by inflating pharyngeal obturator 32. The respiratory fluid is introduced into endotracheal tube 22 and exits directly in the trachea. If endotracheal tube 22 misses the trachea, and enters esophagus 17, then both obturators 30 and 32 may be inflated to seal the trachea. The respiratory fluid is then confined to the portion of the body leading to the lungs and enters generally into larynx 18, and thence, into the trachea and lungs. No resuscitation fluid is expended inflating the stomach and the stomach contents cannot aspirate into the lungs.

Referring now to FIG. 2, there may be seen a pictorial illustration of a preferred embodiment of the present invention. Emergency endotracheal airway 20 includes an expandable tracheal cuff 30 carried by endotracheal tube 22 and an expandable pharyngeal cuff 32 carried by laryngeal tube 26. Laryngeal tube 26 is provided with an outer end 27 and an inner end 28 whereby resuscitation fluid which is introduced into outer end 27 exists through inner end 28. Laryngeal tube 26 passes through pharyngeal cuff 32 and may be sealed about the entrance and exit or may be sealed exteriorly of cuff 32 as cuff 32 expands to surround tube 26. The length of laryngeal tube 26 is preferably about 90–100 mm to obtain a penetration into a patient to a region adjacent the larynx without activating the epiglottis and closing the larynx. A standard tube diameter of 10 mm may be conveniently selected for this tube.

Pharyngeal cuff 32 is formed along laryngeal tube 26 and endotracheal tube 22 and may be sealed about tubes 26 and 22 or may simply seal around tubes 26 and 22 when expanded. Pharyngeal cuff 32 is designed to obturate, or block, the pharyngeal region beneath the oral and nasal openings. Pharyngeal cuff 32 generally takes the form of an expandable element which is generally expanded by inflating with the pressurized fluid. It is desirable that pharyngeal cuff 32 be inflatable at a relatively low pressure, e.g. about 0.5 psi, in order to prevent damage to the surrounding pharyngeal tissue. Pharyngeal cuff 32 may conveniently be formed as a cylinder or a truncated cone in order to completely block the pharyngeal volume into which the cuff 32 is inserted. If a low pressure inflation is used, the surface area of cuff 32 must be sufficient to exert enough total force on the surrounding pharyngeal tissue to limit or prevent the escape of fluids between pharyngeal cuff 32 and the surrounding tissues.

It should be noted that pharyngeal cuff 32 may be bifurcated where a first, low pressure cuff is inflated adjacent the soft oral tissues. A second, higher pressure cuff might then be provided for use in the portion of the pharynx adjacent the larynx. This bifurcated obturator would ensure that proper sealing results.

Referring again to FIG. 2, there is also seen endotracheal tube 22 having tracheal obturator 30 adjacent inner end 24. In one embodiment, endotracheal tube 22 is hollow and inner end 24 defines an opening to the lungs, or to the stomach if used as an esophageal obturator. Thus, the lungs or the stomach region can be accessed through tube 22. Endotracheal tube 22 may also be provided with an indicator device 25 at outer end 23 for indicating the presence of a fluid within tube 22. Such an indicator means may simply take the form of a flexible member which inflates when pressurized by gases and/or other fluids entering endotracheal tube 22 from the lungs or the stomach. If an indicator device is not required, outer end 23 may simply be capped or may even remain open. The total length of endotracheal tube 22 may conveniently be 200–230 mm in order to place inner end 24 positively within the trachea.

Stylet bullet guide 75 is provided for inserting inner end 24 of tube 22 into the trachea. Guide 75 has a cap 78 which rests against the top surface of filling 25 and may serve to seal the interior of tube 22. A stylet or guide portion 76 is formed from a suitable thermoplastic to assume a shape cooperating with the pharynx and larynx to place inner end 24 in the trachea. Bullet 79 protrudes from inner end 24 for non-traumatic insertion of inner end 24. Bullet 79 may be fabricated from a soft, pliant material to minimize any trauma to the vocal cords during traverse of bullet 79. After insertion, bullet 79 and guide 76 are sized to be withdrawn through endotracheal tube 22 and allow access to the lungs. For esphogeal use, stylet guide 75 may remain in place as a seal. A properly shaped stylet 76 generally increases the success rate for blind intubation from 10–20% to about 50%.

Tracheal obturator 30 may be expanded in several ways, both by mechanical mechanisms and by inflation. A variety of obturators are shown in U.S. Pat. No. 3,683,908, and any one of them may be used in conjunction with the present invention. If, however, a low pressure device is chosen for pharyngeal obturator 32, it would be desirable to also provide a low pressure device for tracheal obturator 30 in order that both will inflate and seal at the same pressure. Accordingly, a suitable tracheal obturator would provide sufficient surface area in contact with the interior walls of the trachea or esophagus to exert sufficient force to limit or prevent the passage of fluid between an inflated tracheal obturator 30 and the interior of the trachea or esophagus.

A cuff inflator means 34 is also shown in FIG. 2. Cuff inflator means 34 includes a fluid inlet 36 to which the inflating fluid is introduced. The inflating fluid may pass through check valves 39 and 40 and into tubes 44 and 42, respectively, for inflating pharyngeal cuff 32 and tracheal cuff 30, respectively. Tubes 42 and 44 may conveniently be equipped with pressure indicator balloons 41 and 43 which expand to a diameter somewhat greater than the diameter of tubes 42 and 44 to indicate the presence of pressure within the tubes 42 and 44. A visual observation is thus provided of the presence or absence of pressurizing fluid within expandable cuffs 32 and 30. A pressure relief valve 37 may be included on fluid inlet 36 in order to prevent over-pressurizing expandable cuffs 32 and 30 and subsequent tissue damage.

Alternately, cuff inflator means 34 may simply consist of a fluid inlet 36 interconnected with tubes 42 and 44. Pressure relief valve 37 may be omitted where human breath is being used to inflate cuffs 30 and 32. It has been determined that a maximum pressure of only about 120 cm of $H_2O$ can be obtained where human breath is used, and this pressure will not generally traumatize the tissues surrounding cuffs 30 and 32. If further simplification of cuff inflator means 34 is desired, check valves 39 and 40 may be removed and any convenient external clamp may be employed to prevent the release of pressure from cuffs 30 and 32.

Various alternate means may be provided to inflate cuffs 32 and 30. Individual fluid inlets 36 might be required if expandable cuffs 32 and 30 are designed to require different pressures for proper inflation and sealing. Alternatively, if a single inflation pressure is chosen, it is possible to combine inflation tubes 42 and 44 into a single tube which inflates both pharyngeal cuff 32 and tracheal cuff 30.

Yet another cuff for use as pharyngeal obturator 32 or tracheal obturator 22 embodies a normally expanded material which sealingly engages the pharynx and trachea. The normally expanded material would retract upon the application of a vacuum device for insertion or removal. Once inserted, however, the cuffs remain expanded in the event of any system failures and the emergency resuscitation can continue.

In a preferred embodiment of the present invention, outer end 27 of laryngeal tube 26, outer end 23 of endotracheal tube 22, and fluid inlet 36 are provided with standard 15 mm fittings for interconnecting with commercially-available respiration and inhalation equipment. A suitable tracheal obturator may be spherical or cylindrical, having a diameter of 4–5 mm and a length of about 4 cm. A suitable pharyngeal cuff, as hereinabove discussed, may be provided with a minimum diameter of about 7 cm and a length of about 8 cm. The inflatable cuffs are preferably of a thin, flexible material which does not damage surrounding tissue. Pharyngeal tube 26 and endotracheal tube 22 are preferably formed of a thermoplastic-type material which is flexible but which will retain a permanent set when formed at a selected temperature and thereafter cooled. Thus, these tubes may be curved in a conventional manner to facilitate entry through the oral cavity, with the elongated tracheal tube 22 formed to guide itself into the trachea in cooperation with stylet bullet guide 75.

Referring again to FIG. 2, there is seen face shield 46. Shield 46 is designed to fit over a portion of the face, and more particularly the oral cavity. Shield 46 is sufficiently large that it cannot be accidentally ingested by a patient. Pharyngeal tube 26 and endotracheal tube 22 may be force-fit into face shield 46 to predetermined lengths so that tubes 22 and 26 will be in the correct location when emergency endotracheal airway 20 has been inserted until shield 46 rests adjacent the face of the patient. Pharyngeal tube 26 is conveniently formed to an elevation apart from endotracheal tube 22 in order to insure that there is a positive indication of the identity of the two tubes.

If desired, the outer end 23 of endotracheal tube 22 may be force-fit into shield 46 so that shield 46 may be removed from about outer end 23. Then, when endotracheal tube 22 is inserted into the patient's trachea, shield 46, tracheal tube 26 and pharyngeal cuff 32 may be removed from about endotracheal tube 22 and cuff 30 may be inflated to seal about the interior of the trachea and the respiratory fluid introduced directly through esophageal tube 22. It is anticipated that pharyngeal cuff 32 and laryngeal tube 26 will normally remain in place to back up endotracheal tube 22.

Referring now to FIG. 3, there may be seen a second embodiment of the present invention where all of the tubular members are contained within a single elongated endotracheal tube 66. Elongated endotracheal tube 66 is inserted through face shield 46, protected by teeth shield 47 and is pre-shaped to guide inner end 68 into the trachea. Expandable tracheal cuff may be inflated through tube 42 to effectively block the trachea. Tube 70 is included within endotracheal tube 66 and extends through inner end 68 for communicating with the trachea. Stylet bullet guide 75 (FIG. 2) is inserted within tube 70 for guiding endotracheal tube 66 and inner end 68 into the trachea. A block or dam 71 is contained within esophageal tube 66 at a location above tracheal cuff 60.

Pharyngeal obturator 62 is also attached about endotracheal tube 66 and is inflated by tube 44. Endotracheal tube 66 defines opening 72 adjacent the larynx for introducing respiratory fluid into the laryngeal region between tracheal cuff 60 and pharyngeal cuff 62 if endotracheal tube 66 inadvertently enters the esophagus. A suitable respiratory fluid is introduce through either tube 70 or tube 66.

Cuff inflator means 34 is provided as hereinabove described for inflating tracheal cuff 60 and pharyngeal cuff 62. In this embodiment, inflation tubes 42 and 44 are carried within endotracheal tube 66 and communicate with cuffs 62 and 60 which from within endotracheal tube 66.

The embodiment of the invention depicted in FIG. 3 has an advantage in requiring only one tube to be inserted through the mouth and pharynx and into the trachea. However, it is felt that the apparatus shown in FIG. 3 may be more difficult and expensive to manufacture than the apparatus shown in FIG. 2.

Referring now to FIG. 4, there may be seen yet a third embodiment according to the present invention. Resuscitation apparatus 50 is provided, again having endotracheal tube 52 extending from an outer end 53 to an inner end 54 which may conveniently be open to the trachea and lungs. A laryngeal tube 56 is inserted within endotracheal tube 52 and has an outer end 57 separate from the outher end of endotracheal tube 52. Laryngeal tube 56 extends within endotracheal tube 52 to a location adjacent the larynx and exists endotracheal tube 52 at inner end 58 of laryngeal tube 56. Inner end 58 is sealed from the interior of endotracheal tube 52 so that fluids within endotracheal tube 52 do not enter into laryngeal tube 56. Tracheal obturator 60 and pharyngeal obturator 62 are provided along elongated endotracheal tube 52 as hereinabove described for FIG. 3. Inflation tubes 42 and 44 are shown to be carried internally or endotracheal tube 52 but may be provided externally and in any of the embodiments hereinabove described for FIGS. 1-3.

A cuff inflator means 34 is provided as hereinabove discussed. Further, face shield 46 is again provided to support and position endotracheal tube 52 for inserting into the patient to the proper internal location. The device shown in FIG. 4 has an internal structure which may be more expensive to manufacture than shown in FIG. 2, yet not as expensive to manufacture as that shown in FIG. 3.

In the event of an emergency requiring artificial resuscitation, a medical technician or lay person trained in emergency first-aid should be able to use the apparatus which is the subject of the present invention without undue difficulty. A method using the device depicted in FIG. 2 will be described, although the operation is substantially identical using the apparatus depicted in FIGS. 3 and 4.

In a preferred embodiment, the endotracheal and laryngeal tubes, along with the associated obturators, are pre-coated with a suitable lubricant, which may conveniently be a medical grade silicone, to ease tubular passage through the body regions. Endotracheal tube 22 and laryngeal tube 26 are inserted through the mouth of the patient until face shield 46 is adjacent the face of the patient. Stylet bullet guide 75 serves to guide tube 22 into the trachea. Tracheal obturator 30 is inflated by pressurizing through fluid inlet 36. This pressurizing may conveniently be accomplished by the operator simply blowing into fluid inlet 36, thereby opening check valve 40 and introducing air through inflation line 42 into tracheal obturator 30. Pressure indicator balloon 41 on tube 42 indicates the presence of pressure within the obturator and that inflation has been achieved. Pressure relief valve 37 prevents over-pressurizing the obturator and prevents damage to the surrounding tissue.

The location of inner end 24 of endotracheal tube 22 is then determined. Stylet bullet guide 75 is removed from tube 22 and respiratory fluid is introduced. If chest movement is observed, the blind intubation has been achieved and resuscitation can be commenced. If no chest movement is observed, the pharyngeal obturator 32 is inflated, if not inflated concurrently with obturator 30. The endotracheal tube 22 may be capped to seal the gastric region and respiratory fluid introduced through inner end 28 of laryngeal tube 26.

The operator now introduces respiratory fluid through the outer end 27 of laryngeal tube 26 or endotracheal tube 22 and, thence, into the patient's lungs. The respiratory fluid may be expired air breathed directly into outer ends 27 or 25 by the operator or may be oxygen and/or air mixture introduced through outer ends 27 or 25 by means of automatically controlled respiratory equipment. According to the present invention, there is no requirement that face shield 46 be sealed against the facial contours of the patient and no operator action is required to maintain any such seal. In the event that automatic respiratory equipment is available, the operator is free to attend to other emergency treatment if needed.

If endotracheal tube 22 enters the esophagus, the respiratory fluid is introduced through laryngeal tube 26 after the obturators have been inflated. This will be apparent when respiratory fluid is applied through endotracheal tube 22 and no chest movement results. If this occurs, the respiratory fluid is being introduced through endotracheal tube 22 directly into the gastric region and the emergency resuscitation is discontinued and the pharyngeal obturator 32 is inflated. Obturator 30 then acts to confine the respiratory fluid to the lungs and prevents the entry of any fluid from the stomach into the lungs. However, the present device should successfully intubate in about 50% of the attempts.

Other advantages of the present emergency resuscitation apparatus will be apparent when the patient has suffered severe injury about the face and throat. It is very difficult to seal around the facial contours where the victim has suffered massive facial injuries or where the face has been severely burned. Further, the pharyngeal tissues are easily susceptible to injuries and subsequent bleeding in that region can interfere with rescuscitation of the victim. The use of a pharyngeal obturator serves to exert pressure against ruptured blood vessels within the pharynx and to stop such bleeding. Further, there is no requirement with the present invention that any sealing be accomplished about the facial contours of the patient.

Yet another advantage of the present invention is obtained where the endotracheal tube has been inserted in the esophagus. The large lumen provided for introducing respiratory fluid into the trachea serves to vent any respiratory fluid which leaks between the tracheal obturator now sealing against the esophagus. Thus, the stomach region remains unpressurized and less subject to aspirating the contents.

It is therefore apparent that the present invention is one wall adapted to attain all of the objects and advantages hereinabove set forth, together with other advantages which will become obvious and inherent from a description of the apparatus itself. It will be understood that certain combinations and subcombinations are of utility and may be employed without reference to other features and subcombinations. This is contemplated by and is within the scope of the present invention.

What is claimed is:

1. An emergency endotracheal airway, comprising:
    a first expandable member and means for inflating said first expandable member by at least human breath to a volume effectively filling a pharyngeal region adapted to continuously seal both the oral and nasal passages extending therefrom;
    an endotracheal tube extending through said first expandable member and having an outer opening above said first expandable member and an inner opening below said first expandable member adapted to terminate in a trachea,
    a second expandable member and means for inflating said second expandable member by at least human breath surrounding said endotracheal tube adjacent said inner opening and adapted to continuously seal against a wall portion of said trachea,
    a laryngeal tube extending through said first expandable member and having an outer opening adapted to receive a supply of a selected fluid and an inner opening below said first expandable member adapted to terminate in a laryngeal region above said second expandable member; and
    a stylet removably inserted through said endotracheal tube and having a predetermined curvature and one rounded end adapted to guide said inner opening of said endotracheal tube into the trachea during insertion thereof,
    whereby when said endotracheal tube is properly inserted into said trachea, a patient can be ventilated by inflating said second expandable member and, if desired, said first expandable member, and administering gas to the patient's lungs via said endotracheal tube, and if said endotracheal tube is accidentially inserted into the patient's esophagus, the patient can be ventilated by inflating said first and second inflatable members and administering gas to the patient's lungs via said laryngeal tube.

2. An emergency endotracheal airway as described in claim 1, wherein said endotracheal tube further includes indicator meand cooperating with said outer opening of said endotracheal tube to signal the presence of fluid within said endotracheal tube.

3. An emergency endotracheal airway as described in either in claim 1 or 2, further including:
    a shield surrounding said endotracheal tube and said laryngeal tube adapted to position said tubes within a patient and protect said tubes from penetration by teeth.

4. An emergency endotracheal airway as described in claim 3, further including:
    valve means communicating with said first and second expandable members for maintaining inflation pressures, and
    means for indicating the presence of greater than atmospheric pressure in said first and second expandable members.

* * * * *

UNITED STATES PATENT AND TRADEMARK OFFICE
CERTIFICATE OF CORRECTION

PATENT NO. : 4,231,365
DATED : November 4, 1980
INVENTOR(S) : Eugene N. Scarberry It is certified that error appears in the above-identified patent and that said Letters Patent are hereby corrected as shown below:

Col. 9, line 4, "wall" should be --well--;

Col. 10, line 18, "meand" should be --means--.

Insert claims 5, 6 and 7.

5. An emergency endotracheal airway as described in Claim 1, wherein said endotracheal tube and said laryngeal tube are adjacent one another.

6. An emergency endotracheal airway as described in Claim 1, wherein said endotracheal tube includes a portion within said laryngeal tube.

7. An emergency endotracheal airway as described in Claim 1, wherein said laryngeal tube includes at least a portion within said endotracheal tube.

On the title page "4 Claims" should read --7 Claims--.

Signed and Sealed this

Sixteenth Day of June 1981

[SEAL]

Attest:

RENE D. TEGTMEYER

Attesting Officer     Acting Commissioner of Patents and Trademarks